United States Patent [19]

Mochizuki et al.

[11] Patent Number: 4,958,130
[45] Date of Patent: Sep. 18, 1990

[54] EVALUATION METHOD OF CORROSION OF STEEL MATERIAL EMBEDDED IN CONCRETE

[75] Inventors: Noriyasu Mochizuki, Hannou; Hiroji Nakauchi, Okegawa, both of Japan

[73] Assignee: Nakagawa Corrosion Protecting Co., Ltd., Tokyo, Japan

[21] Appl. No.: 327,992

[22] Filed: Mar. 23, 1989

[30] Foreign Application Priority Data

Apr. 4, 1988 [JP] Japan .................................. 63-81347

[51] Int. Cl.$^5$ ............................................. G01N 17/02
[52] U.S. Cl. .................................. 324/700; 204/153.11
[58] Field of Search .................. 324/65 CR, 71.2, 700; 204/1 C, 404

[56] References Cited

U.S. PATENT DOCUMENTS

| | | | |
|---|---|---|---|
| 4,080,565 | 3/1978 | Polak et al. | 204/1 C |
| 4,130,464 | 12/1978 | Kanno et al. | 204/404 |
| 4,217,544 | 8/1980 | Schmidt | 204/404 |
| 4,575,678 | 3/1986 | Hladky | 324/71.2 |
| 4,587,479 | 5/1986 | Rhoades et al. | 324/65 CR |

FOREIGN PATENT DOCUMENTS

173451 9/1985 Japan .................................. 324/65 R

Primary Examiner—Reinhard J. Eisenzopf
Assistant Examiner—Maura K. Regan
Attorney, Agent, or Firm—Bucknam and Archer

[57] ABSTRACT

An evaluation method of corrosion of a steel material in a concrete. The evaluation is made by use of three parameters, i.e., the corrosion potential, the polarization resistance and the concrete resistance measured for plurality of measuring points on the concrete over the steel material. The values of polarization resistance and the concrete resistance are used after converting them to the value per unit area and unit length, thereby quantitative absolute evaluation being made without depending on the ambient conditions. The measured values of each parameter are classified to several zones by threshold value, and the results thereof are collectively took into consideration for the evaluation. The parameters and/or the threshold values are compensated in connection with temperature in view of accuracy.

3 Claims, 8 Drawing Sheets

FIG. 2A

FIG. 2B $R_S(20)$: calibrated value of concrete resistance at 20°C $R_S(t)$: Rs in environment temperature of t °C temperature (°C)
RH = 80%
○ : no corrosion
△ : mild corrosion
□ : severe corrosion

- severe corrosion
- mild corrosion
- no corrosion

●: severe corrosion
♦: mild corrosion
o: no corrosion

F I G. 8

EVALUATION METHOD OF CORROSION OF STEEL MATERIAL EMBEDDED IN CONCRETE

BACKGROUND OF THE INVENTION 1. (Field of the Invention)

This invention relates to an evaluation method of corrosion of a steel material embedded in a concrete which evaluates the corrosion state of the steel material in a reinforced concrete (RC) structure on the basis of three parameters, i.e., corrosion potential measured by one or more reference electrodes locatable or disposed on the concrete surface, the actually measured values of polarization resistance and concrete resistance (liquid resistance) that are measured by applying currents between one or more sensors locatable or disposed on the concrete surface and the steel material, and more particularly to an evaluation method of corrosion of a steel material inside a concrete which makes it possible to make absolute evaluation of the corrosion state and to improve the evaluation accuracy.

2. (Prior Art)

The problem of corrosion of a steel material in concrete is one of the most critical problems relating to durability of a concrete structure and various researches have so far been made for establishing evaluation methods of the corrosion state. Among them, non-destructive evaluation methods of corrosion state include a method which measures corrosion potential (in accordance with the ASTM standards) on the concrete surface, a method which judges the occurrence of corrosion from the result of observation with eyes, a method which measures the polarization resistance by applying currents between electrodes disposed on the concrete surface and the steel material inside the concrete, and diagnoses corrosion on the basis of the measurement results, and a method which measures corrosion potential and concrete resistance together with the polarization resistance, and examines collectively the corrosion state on the basis of these results (Japanese Patent Laid-Open No. 217147/1984). Furthermore, there is a method which conducts a neutralization test and a method which judges the corrosion state by measuring the decrease in diameter of a steel bar by a pacometer.

Destructive methods which involve destruction of the concrete includes a method which chips the concrete cover and observes the sample with eyes, a method which measures salt concentration, and the like.

However, the method described above which measures the corrosion potential, the polarization resistance or the concrete resistance handles merely the measurement values themselves and involves the problem that relative comparison can be made only under the same boundary condition, the method cannot make absolute evaluation. Since these objects being measured change with the boundary condition or with a temperature, it involves another problem that its evaluation accuracy is low.

On the other hand, the method which relies on the mere observation with the eyes involves the problem that evaluation can be made only after corrosion has considerably proceeded to some extent as to provide a rusty solution and rusty cracks on the surface of the concrete. The neutralization test method cannot recognize the corrosion in the case of progress of corrosion by salts and the test itself becomes meaningless. In the case of the method which measures the diameter of the reinforcing steel by the pacometer, no pacometer capable of measuring the diameter with accuracy of below 0.1 mm is available at present, and this method cannot detect corrosion of the reinforcing steel inside the concrete wherein cracks in the axial direction are believed to occur by the reduction of thickness of below 0.1 mm.

Furthermore, the method by salt concentration measurement and the direct and high accurate method involving chipping have the drawback that they involve destruction. The salt concentration measurement method is after all environmental evaluation and does not directly relate to corrosion evaluation of the reinforcing steel.

In view of these problems with the prior art methods, this invention contemplates to provide an evaluation method of steel material corrosion which can make quantitative, highly accurate and more detailed evaluation of not only the corrosion state at the present but also the corrosion progress in the future without being affected by the environmental condition.

SUMMARY OF THE INVENTION

Figure 1:
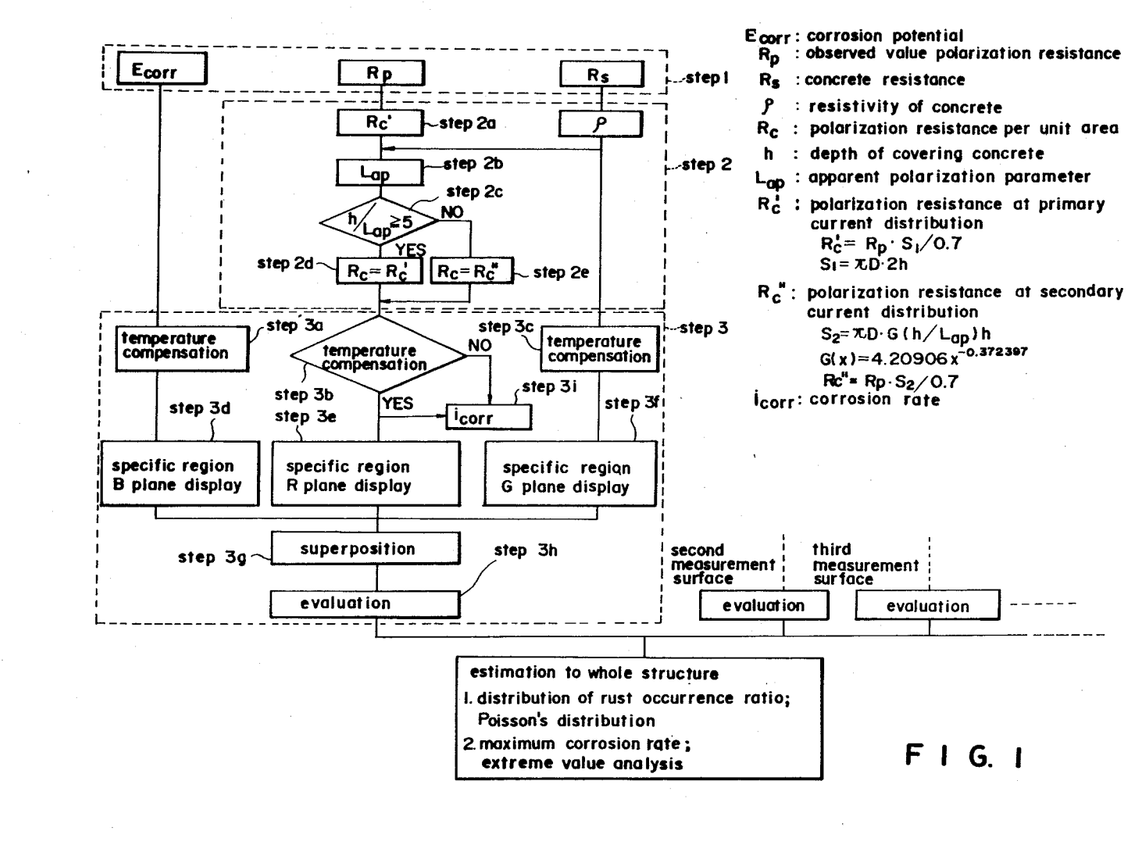
FIG. 1 is a flowchart showing the procedures of reinforcing steel corrosion diagnosis data analysis in accordance with the evaluation method of corrosion of steel material in a concrete in accordance with the present invention.

The evaluation method of steel material corrosion inside the concrete in accordance with the present invention comprises as shown in FIG. 1:

a step (step 1) of measuring a corrosion potential $E_{corr}$ at each of a plurality of measuring points on the surface of the concrete positioned over the steel material by use of a reference electrode locatable or disposed at each measuring point and causing a current to flow between a sensor, which includes a counter electrode and reference electrode locatable or disposed at each of the plurality of measuring points, and the steel material to measure a polarization resistance $R_p$ and a concrete resistance $R_s$ at each measuring point;

a step (step 2) of converting the observed values of the polarization resistance $R_p$ and concrete resistance $R_s$ measured at each of the measuring points to a real polarization resistance $R_c$ and resistivity $\rho$ which are the resistance values per unit area and unit length by use of a formula derived in advance from analytical results of current distribution and experimental formulas; and a step (step 3) of evaluating the state of corrosion of the steel material on the basis of the corrosion potential measured for each measuring point and on the basis of the real polarization resistance $R_c$ and resistivity $\rho$.

Furthermore, the step 3 described above includes preferably steps (steps 3a–3c) of unifying or calibrating the corrosion potential $E_{corr}$ measured for each of the measuring points, the polarization resistance $R_c$ and resistivity $\rho$ that are converted from the observed values measured at each of the measuring points, and and/or threshold values for evaluating dividedly in such a manner that the values thereof become values at a predetermined reference temperature; and steps (steps 3d–3h) of evaluating the state of corrosion of the steel material at each measuring point in accordance with corrosion evaluation reference obtained by zoning the corrosion potential $E_{corr}$, the polarization resistance $R_c$ and resistivity $\rho$ for each measuring point on the basis of the threshold values.

Here, the actually measured polarization resistance value $R_p$ and the concrete resistance $R_s$ at the step 1 can be obtained by measuring the impedance, that is, the sum $(R_p + R_s)$ of the polarization resistance and the concrete resistance, when a current of 0.01 Hz, for example, is caused by current flow between the sensor and the steel material such as the reinforcing steel, and the impedance, that is, the concrete resistance $R_s$, when a current of 10 KHz is applied.

As the formula for converting the concrete resistance $R_s$ to the resistivity $\rho$ at the step 2, it is possible, for example, to use the formulas shown in Table 1.

TABLE 1

| | $l/h \leq 4$ | |
|---|---|---|
| | $h/a < 1$ | $h/a \geq 1$ |
| | $\rho = \dfrac{R_s a^{1.37}}{0.44 h^{0.37}}$ | $\rho = \dfrac{R_s a^{1.085}}{0.43 h^{0.085}}$ |

| | $l/h > 4$ | | |
|---|---|---|---|
| | | $h/D$ | |
| a/D | $h/D < 2$ | $2 \leq h/D \leq 4$ | $h/D > 4$ |
| $a/D < 2$ | $\rho = \dfrac{R_s a^{1.30}}{0.472 h^{0.01} D^{0.29}}$ | $\rho = \dfrac{R_s a^{1.15}}{0.501 h^{0.01} D^{0.14}}$ | $\rho = \dfrac{R_s a^{0.98} D^{0.03}}{0.465 h^{0.01}}$ |
| $2 \leq a/D \leq 3$ | $\rho = \dfrac{R_s a^{1.30}}{0.504 h^{0.08} D^{0.22}}$ | $\rho = \dfrac{R_s a^{1.15}}{0.515 h^{0.08} D^{0.07}}$ | $\rho = \dfrac{R_s a^{0.98} D^{0.10}}{0.477 h^{0.08}}$ |
| $a/D > 3$ | $\rho = \dfrac{R_s a^{1.30}}{0.488 h^{0.21} D^{0.09}}$ | $\rho = \dfrac{R_s a^{1.15} D^{0.06}}{0.500 h^{0.21}}$ | $\rho = \dfrac{R_s a^{0.98} D^{0.23}}{0.475 h^{0.21}}$ |

$\rho$: resistivity
h: depth of concrete cover
$R_s$: electrical resistance (environment resistance)
D: diameter of reinforcing steel
a: sensor diameter
l: gap between reinforcing steels The formulas shown in Table 1 include depth of concrete cover h, the diameter D of the reinforcing steel, the sensor diameter a and the gap l between the reinforcing steels and are determined experimentally in advance in consideration of these parameters. The following formulas (1) through (3), for example, can be used as the formula for converting the polarization resistance actually measured value $R_p$ to the real polarization resistance $R_c$.

$$R_c' = R_p \cdot \pi D \cdot 2h / 0.7 \quad (1)$$

$$L_{ap} = R_c' / \rho \quad (2)$$

$$h / L_{ap} < 5 : R_c = R_p \cdot \pi D \cdot G (h / L_{ap}) \cdot h / 0.7 \quad (3)$$

$$h / L_{ap} \geq 5 : R_c = R_c'$$

$R_c'$ : apparent polarization resistance
$R_p$ : actually measured value of polarization resistance
D : diameter of reinforcing steel
h : depth of concrete cover
$L_{ap}$ : apparent polarization parameter
$\rho$ : resistivity of concrete
$R_c$ : real polarization resistance $G(x) = a x^b$ $a = 4.20906$ $b = -0.372397$ These formulas are obtained from the experimental results representing that the area of the reinforcing steel may be calculated under the estimation that 70% of the total current flowing between the sensor and the reinforcing steel flows through the outer reinforcing steel (the reinforcing steel closest to the concrete surface) contained inside the area circled with the radius of the depth of concrete cover h from the center of the sensor (formula (1) or inside the radius considering the polarization parameter in addition to the above, (formula 3).

As shown in FIG. 1, the step 2 in this case includes the step (step 2a) of obtaining the apparent polarization resistance $R_c'$ from the actually measured polarization resistance value $R_p$, the step (step 2b) of obtaining the apparent polarization parameter $L_{ap}$ by dividing the apparent polarization resistance $R_c'$ by the resistivity $\rho$, the step (step 2c) of judging whether or not the value (h/$L_{ap}$) obtained by dividing the depth of concrete cover h of the steel material by the polarization parameter $L_{ap}$ is not less than a predetermined value such as 5, the step (step 2d) of regarding the apparent polarization resistance $R_c'$ as the real polarization resistance $R_c$ when this value is not less than 5 and the step (step 2e) of determining the real polarization resistance $R_c$ from the actually measured polarization resistance value $R_p$ in consideration of h/$L_{ap}$ when the value (h/$L_{ap}$) is less than 5. The polarization resistance $R_c$ thus determined can be converted to corrosion rate $i_{corr}$ ($= K/R_c$) by a constant K (step 3i).

When the evaluation of the corrosion state is made at the step 3, the evaluation can be made conveniently if each region classified by the threshold value of each of the parameters, i.e., the corrosion potential $E_{corr}'$ the polarization resistance $R_c$ and the resistivity $\rho$, is displayed in superposition in such a manner as to correspond to each measuring point. For example, red, green and blue are set respectively to three regions each of which is one of the two regions separated by corresponding threshold value of each parameter and outputted to the R, G and B planes of a personal computer (steps 3d–3f), and each plane is superposed and displayed on a display (step 3g) so that the evaluation can be made (step 3h). In this case, the eight regions determined by the combination of the parameters can be displayed at the same time, and the position with respect to the measuring point, area, etc., of each region can be calculated at a moment by the personal computer by surveying the color information of each dot displayed and counting the number of dots for every colors. More detailed evaluation can be made by setting two or more threshold values for each parameter in place of only single threshold value and conducting similar superposition a plurality of times.

Among the three parameters described above, the corrosion potential $E_{corr}$ and the polarization resistance $R_c$ are the parameters for estimating the corrosion state of the steel material at the present time and the resistivity $\rho$ is the parameter for evaluating corrosiveness of the environment. As will be described later, the greater the number of the parameters, the higher becomes accuracy of the corrosion evaluation. Furthermore, in the binary system consisting of factors, other than resistivity $\rho$, such as $E_{corr}$ and $R_c$, it is not possible to diagnose the occurrence of corrosion in future by salts which could not be anticipated from the present situation in corrosion, and to make diagnosis from this aspect, the evaluation by the ternary system such as that of the present invention inclusive of resistivity $\rho$ as the parameter for evaluating the environment is essential.

Figure 2A:
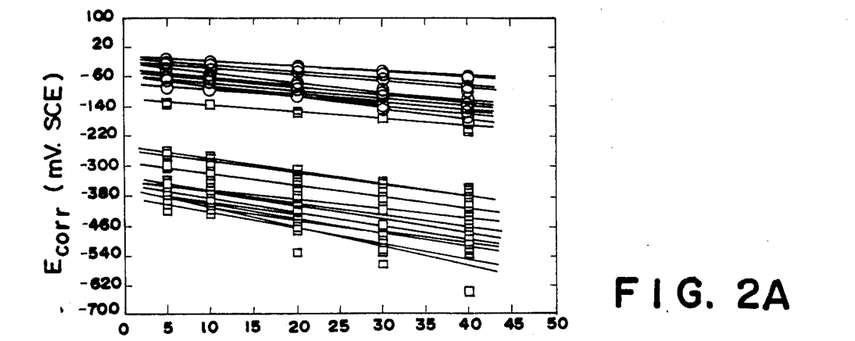
FIGS. 2A–2C are diagrams showing temperature dependence of a corrosion potential $E_{corr}$, a polarization resistance $R_c$ and a concrete resistance $R_s$.
Figure 2B:
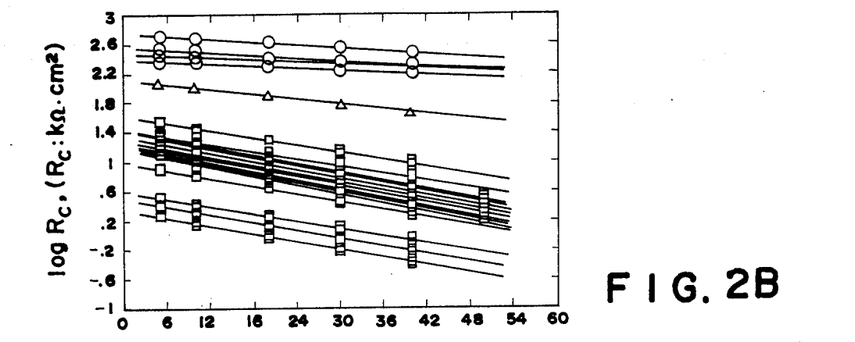
Figure 2C:
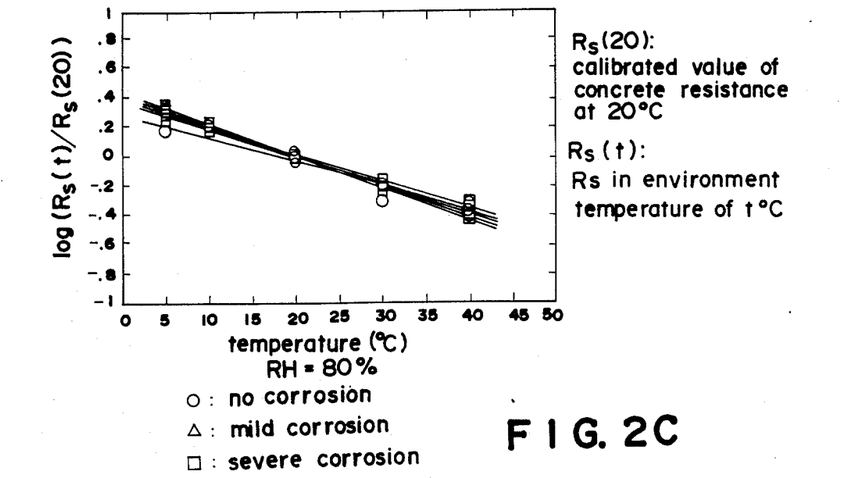

FIG. 2 is a diagram showing temperature dependence of each parameter. As shown in the diagram, each parameter changes considerably with the temperature. Therefore, evaluation accuracy can be improved by converting each parameter or its threshold value to a value at a predetermined reference temperature such as the temperature when the threshold value is set or when each parameter is measured.

In the manner described above, the evaluation method of the present invention uses the measured values of the polarization resistance and concrete resistance by normalizing them to values per unit area and per unit length, and hence, the method of the invention can make absolute evaluation without being affected by the boundary condition. It is also possible to convert the normalized polarization resistance to the corrosion rate and to use it for the absolute evaluation of the corrosion rate.

Evaluation of the corrosion state of a structure as a whole such as the determination of a distribution of rust occurrence ratios, or the analysis of the extreme value of the maximum corrosion rate can be made by applying the evaluation method of the present invention to a plurality of testing area on the surfaces of the structure and gathering these evaluation results.

In accordance with the present invention described above, in a method of evaluating corrosion of the steel material inside the concrete which evaluates the corrosion state of the steel material in the reinforced concrete (RC) structure on the basis of the three parameters, i.e., the corrosion potential, the polarization resistance actually measured value and the concrete resistance, the method of the present invention converts the polarization resistance actually measured value and the concrete resistance to the resistance values per unit area and per unit length and uses them for evaluation. Accordingly, the method of the invention can make quantitative absolute evaluation without depending on the environmental condition and can further improve evaluation accuracy by taking the temperature change of each parameter into consideration. Absolute evaluation of the corrosion speed can be made by converting the normalized polarization resistance to the corrosion rate.

DESCRIPTION OF THE PREFERRED EMBODIMENTS

Hereinafter, an embodiment of the present invention will be described with reference to the drawings.

Absolute corrosion evaluation was carried out for a reinforced concrete (RC) structure in an actual environment by use of a personal computer in accordance with the above-mentioned measurement procedures described with reference to FIG. 1. When the polarization resistance $R_p$ was measured at the step 1, however, it was measured when a current of 0.01 Hz was applied. At the step 3, all of the parameters, i.e., the corrosion potential $E_{corr}$, the polarization resistance $R_c$ and resistivity $\rho$, were converted to the values at a reference temperature of 10° C.

Figure 3:
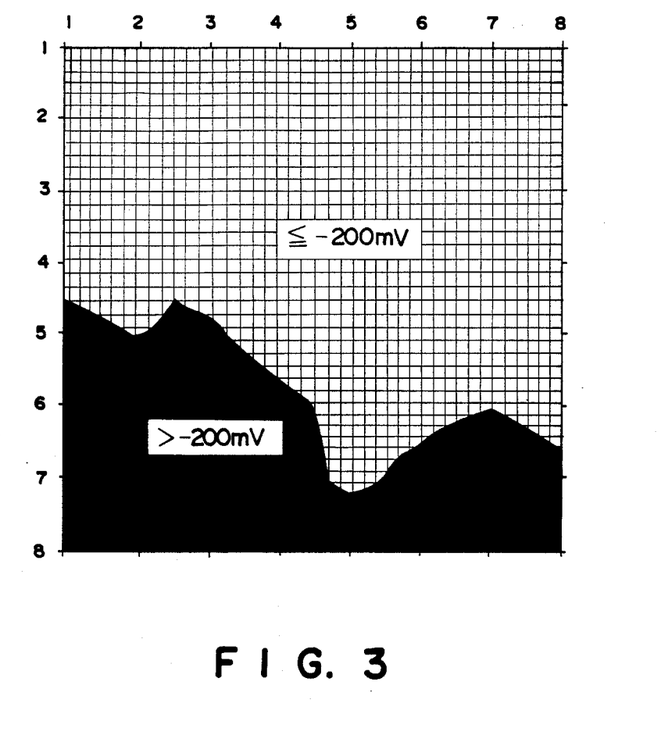
FIGS. 3 to 5 are schematic views showing the region divided by the threshold value of each of the corrosion potential $E_{corr}$, polarization resistance $R_c$ and resistivity $\rho$ measured in accordance with the procedures of FIG. 1 when it is displayed in each of R, G and B planes.
Figure 4:
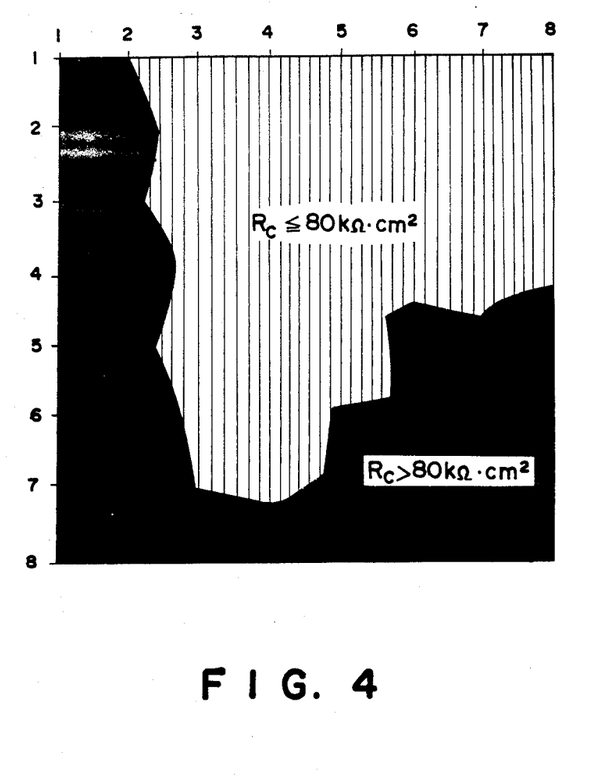
Figure 5:
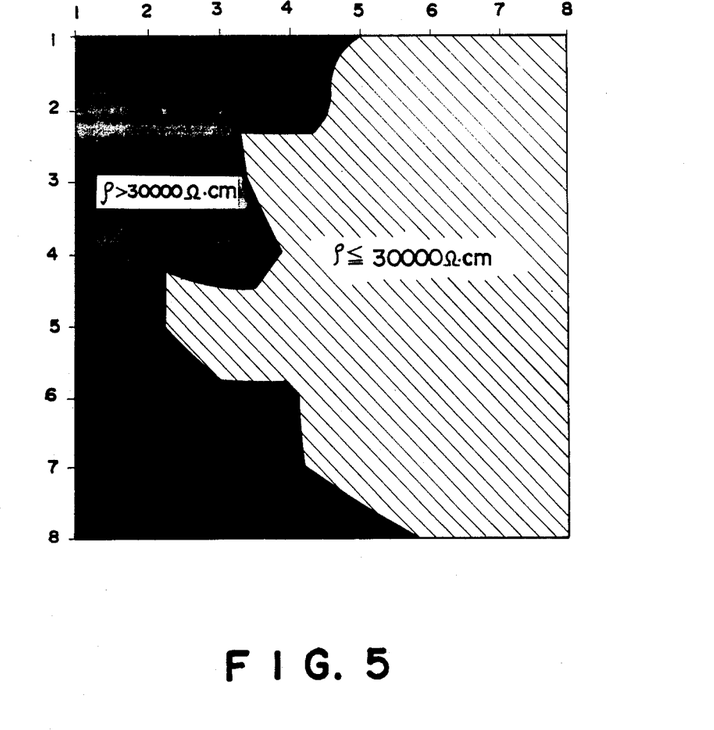

FIG. 3 shows the state where the region of the corrosion potential $E_{corr}$ no more than $-200$ mV, measured hereby and compensated regarding temperature, that is, by use of the threshold value of $-200$ mV at 10° C. for the corrosion potential, is painted in the B (blue) plane of a personal computer. FIGS. 4 and 5 show the state where the regions below the threshold values of 80 KΩ cm2 for the polarization resistance and 30,000 Ω cm for the resistivity $\rho$ are painted in the R (red) and G (green) plane, respectively.

Figure 6:
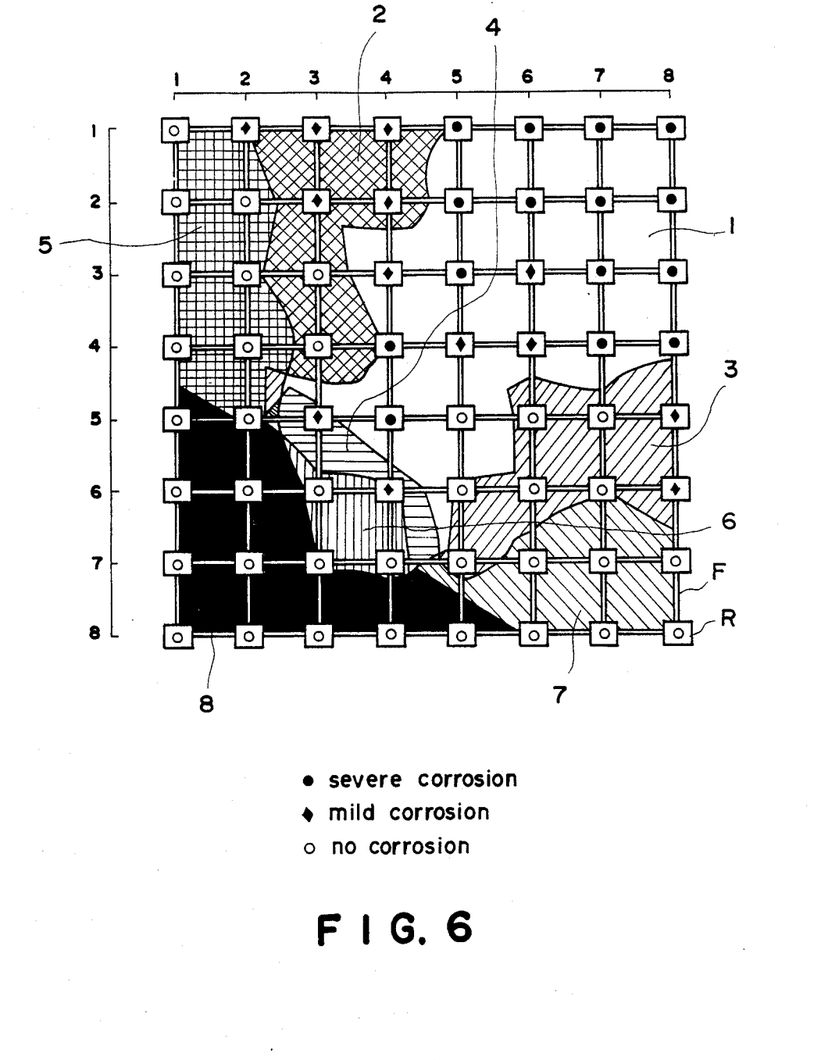
FIG. 6 is a schematic view showing the state when the R, G and B planes of FIGS. 3 to 5 are displayed in superposition.

FIG. 6 shows the planes shown in FIGS. 3 to 5 in superposition with the state of arrangement of reinforcement and the evaluation result of the corrosion state. In the drawing, F represents the reinforcing steel and the square R at each point of intersection of the reinforcing steels F represents the measuring point of each parameter. A black circle, a rhomb and a open circle marks in the squares represent the result of qualitative evaluation of the corrosion state of the reinforcing steels contained in the circle having the radius of the same dimension as the depth of the concrete cover and having the center point same as each measuring point by the observation with eyes by chipping and they represent great corrosion, mild corrosion and no corrosion, respectively. Table 2 represents the result of determination of the proportion to the total area, that is, the area ratio of each of the eight regions determined by the combination of the regions divided by the threshold value of each parameter. Reference numerals 1 through 8 in FIG. 6 represent the regions of the class Nos. 1 through 8 of Table 2, respectively.

TABLE 2

| Classification No. | (3 parameters) | | | Color | Area ratio |
| --- | --- | --- | --- | --- | --- |
| | $E_{corr}$ (mV · SCE) | $R_c$ (KΩ · cm²) | ρ (Ω · cm) | | |
| 1 | ≦ −200 | ≦ 80 | ≦ 30000 | White | 36.1 |
| 2 | ≦ −200 | ≦ 80 | > 30000 | Violet | 11.1 |
| 3 | ≦ −200 | > 80 | ≦ 30000 | Light blue | 11.3 |
| 4 | > −200 | ≦ 80 | ≦ 30000 | Yellow | 3.1 |
| 5 | ≦ −200 | > 80 | > 30000 | Blue | 10.5 |
| 6 | > −200 | ≦ 80 | > 30000 | Red | 3.9 |
| 7 | > −200 | > 80 | ≦ 30000 | Green | 9.0 |
| 8 | > −200 | > 80 | > 30000 | Black | 15.0 |

As can be understood from FIG. 6 and Table 2, the portions where corrosion is great concentrate on the region 1 and the region 8 can be defined as the region where no corrosion is observed, on the contrary. In the other regions, at least one of the three parameters is not more than the threshold value even if mild corrosion exists or even if corrosion does not occurs and it is believed reasonable to judge that the concrete structure is under the influences of injury by salts.

Figure 7A:
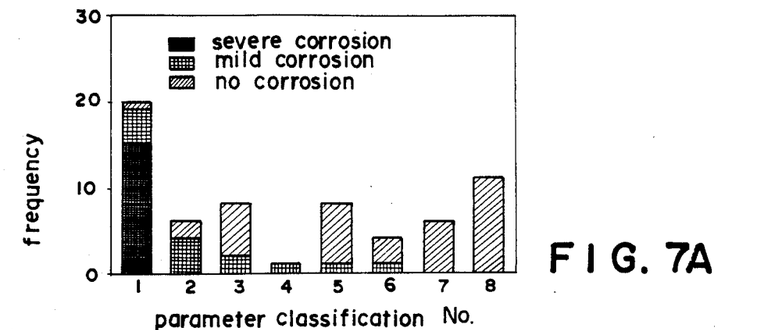
FIG. 7(a) is a diagram showing the frequency distribution of corrosion evaluation in each region of FIG. 6.
Figure 7B:
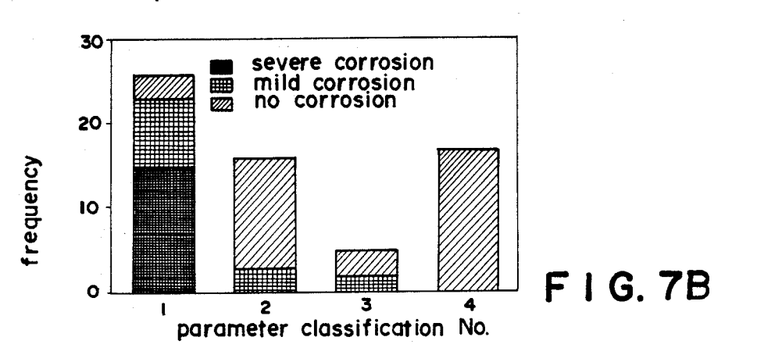
FIG. 7(b) is a diagram showing the frequency distribution corresponding to the evaluation by use of two parameters of the corrosion potential $E_{corr}$ and the polarization resistance $R_c$.
Figure 7C:
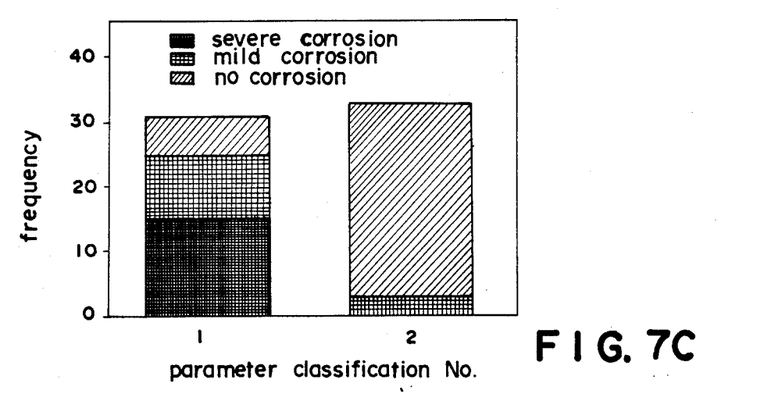
FIG. 7(c) is a diagram showing the frequency distribution corresponding to the evaluation by use of only one parameter of the polarization resistance $R_c$.

FIG. 7(a) is a diagram showing the frequency distribution of the corrosion evaluation in each region shown in FIG. 6. FIG. 7(b) is a diagram showing the frequency distribution corresponding to the evaluation by use of the two parameters of the corrosion potential $E_{corr}$ and the polarization resistance $R_c$ and FIG. 7(c) shows the frequency distribution corresponding to the evaluation by use of only one parameter of the polarization resistance $R_c$. The regions corresponding to the parameter classification number plotted on the abscissa in FIGS. 7(a) through 7(c) are defined by the threshold value of each parameter as shown in Tables 3 to 5.

TABLE 3

| Classification No. | (3 parameters, 10° C.) | | |
| --- | --- | --- | --- |
| | $E_{corr}$ (mV · SCE) | $R_c$ (KΩ · cm2) | ρ (Ω · cm) |
| 1 | ≦ −200 | ≦ 80 | ≦ 30000 |
| 2 | ≦ 200 | ≦ 80 | > 30000 |
| 3 | ≦ −200 | > 80 | ≦ 30000 |
| 4 | > −200 | ≦ 80 | ≦ 30000 |
| 5 | ≦ −200 | > 80 | > 30000 |
| 6 | > −200 | ≦ 80 | > 30000 |
| 7 | > −200 | > 80 | ≦ 30000 |
| 8 | > −200 | > 80 | > 30000 |

TABLE 4

| Classification No. | (2 parameters, 10° C.) | |
| --- | --- | --- |
| | $E_{corr}$ (mV · SCE) | $R_c$ (KΩ · cm²) |
| 1 | ≦ −200 | ≦ 80 |
| 2 | ≦ −200 | > 80 |
| 3 | ≦ −200 | ≦ 80 |
| 4 | > −200 | > 80 |

TABLE 5

| Classification No. | 1 parameter, 10° C. |
| --- | --- |
| | $R_c$ (KΩ · cm²) |
| 1 | ≦ 80 |
| 2 | > 80 |

As can be understood from FIGS. 7(a) to 7(c), the evaluation using the three parameters can detect the corrosion zone and the non-corrosion zone more accurately than the evaluation using one or two parameters.

Figure 8:
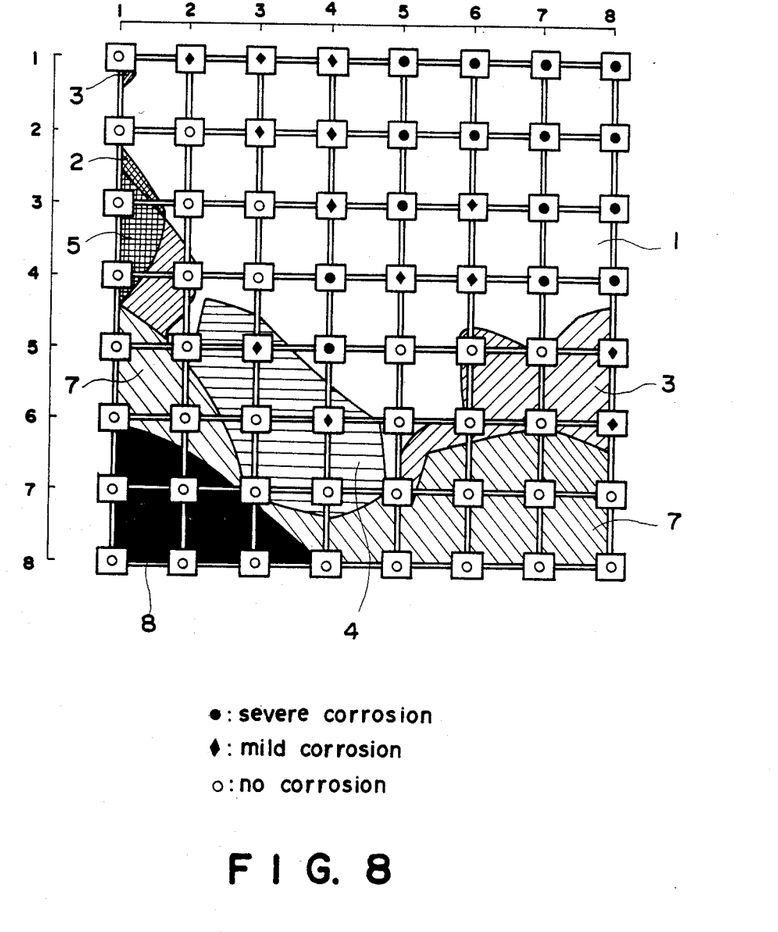
FIG. 8 is a diagram showing the evaluation result when the value at 23° C. at the time of measurement is as such used without making the temperature compensation at the step 3 and corresponding to FIG. 6.

FIG. 8 and Table 6 correspond to FIG. 6 and Table 2, respectively, and represent the results when the values at 23° C. at the time of measurement are used as such without making the temperature compensation at the step 3.

TABLE 6

| Classification No. | (3 parameters) | | | Color |
| --- | --- | --- | --- | --- |
| | $E_{corr}$ (mV · SCE) | $R_c$ (KΩ · cm²) | P (Ω · cm) | |
| 1 | ≦ −200 | ≦ 80 | ≦ 30000 | White |
| 2 | ≦ −200 | ≦ 80 | > 30000 | Violet |
| 3 | ≦ −200 | > 80 | ≦ 30000 | Light blue |
| 4 | > −200 | ≦ 80 | ≦ 30000 | Yellow |
| 5 | ≦ −200 | > 80 | > 30000 | Blue |
| 6 | > −200 | ≦ 80 | > 30000 | Red |
| 7 | > −200 | > 80 | ≦ 30000 | Green |
| 8 | > −200 | > 80 | > 30000 | Black |

As can be understood from FIGS. 8 and 6, correspondence between the actual corrosion state and each region of FIG. 8 provides lower accuracy in comparison with the result shown in FIG. 6 and it is thus possible to confirm the importance of the temperature compensation at the step 3.

What is claimed is:

1. An evaluation method of corrosion of a steel material embedded in a concrete comprising:

the step of measuring a corrosion potential $E_{corr}$ of the steel material at each of a plurality of measuring points on the surface of the concrete positioned over the steel material by use of a reference electrode locatable or disposed at each measuring point, and of measuring the polarization resistance $R_p$ of the steel material and the concrete resistance $R_S$ at each measuring point by applying electric current to the steel material through a sensor including a counter electrode and a reference electrode locatable or disposed at each of said plurality of measuring points; the step of converting the measured values of said polarization resistance $R_p$ and concrete resistance $R_S$ at each of said measuring points to a real polarization resistance $R_c$ and resistivity ρ of the concrete; and a step of evaluating the state of corrosion of said steel material on the basis of and by combining three parameters, at each measuring point, of said corrosion potential $E_{corr}$, real polarization resistance $R_c$ and resistivity ρ.

2. The evaluation method of corrosion of a steel material embedded in a concrete according to claim 1, wherein said step of evaluating the state of corrosion includes:

a step of calibrating all of said corrosion potential $E_{corr}$, real polarization resistance $R_c$ and resistivity ρ at each of said measuring points and/or threshold values for estimating corrosion to the values at predetermined reference temperature; and a step of evaluating the state of corrosion of said steel material at each measuring point in accordance with the standards for corrosion evaluation classified by zoning said corrosion potential $E_{corr}$, polarization resistance $R_c$ and resistivity ρ at each measuring point on the basis of said threshold values.

3. The evaluation method of corrosion of a steel material embedded in a concrete according to claim 1, wherein the steel material is a plurality of reinforcing steels, and the conversion of the polarization resistance $R_p$ and concrete resistance $R_S$ into the real polarization resistance $R_c$ and resistivity $\rho$ is made by use of the values of depth concrete cover h, the diameter D of the reinforcing steel, the sensor diameter a and the gap Q between the adjacent reinforcing steels.

* * * * *